United States Patent [19]
Soza

[11] Patent Number: 6,104,820
[45] Date of Patent: Aug. 15, 2000

[54] MUSICAL MASSAGER

[76] Inventor: Gersan Soza, 3131 Eglinton Avenue East #312, Scarborough, Ontario, Canada, M1J 2G6

[21] Appl. No.: 09/061,161

[22] Filed: Apr. 16, 1998

[51] Int. Cl.[7] .............................. H04R 25/00; A61H 1/00
[52] U.S. Cl. ......................... 381/151; 381/109; 381/124; 601/46; 601/47; 601/49; 607/2
[58] Field of Search .................. 601/46, 47, 49, 601/70, 71, 72, 79, 80, 81, 86, 87; 381/109, 124, 151; 607/1–3

[56] References Cited

U.S. PATENT DOCUMENTS

| | | | |
|---|---|---|---|
| 4,240,437 | 12/1980 | Church | 607/72 |
| 4,779,615 | 10/1988 | Frazier | 601/47 |
| 5,437,607 | 8/1995 | Taylor | 601/49 |
| 5,462,515 | 10/1995 | Tseng | 601/49 |
| 5,524,056 | 6/1996 | Killion et al. | 381/312 |
| 5,542,907 | 8/1996 | Chou | 601/49 |
| 5,553,148 | 9/1996 | Werle | 381/151 |
| 5,611,771 | 3/1997 | Taylor | 601/70 |
| 5,755,676 | 5/1998 | Chen | 601/82 |
| 5,807,287 | 9/1998 | Cheng | 601/49 |
| 5,857,985 | 1/1999 | Feng | 601/47 |
| 5,868,687 | 2/1999 | Tedesco | 601/49 |

FOREIGN PATENT DOCUMENTS 60-204194  10/1985  Japan ........................ 601/47

*Primary Examiner*—Forester W Isen
*Assistant Examiner*—Xu Mei

[57] ABSTRACT

A massaging musical device is provided including a music source adapted to generate a musical electric signal corresponding to music at an output thereof. A listening mechanism is adapted to be situated adjacent ears of a user and releasably connected to the music source for allowing the user to listen to the music. At least one pad is included for subjecting human muscle tissue to the musical electric signal. A control unit includes a timer connected between the music source and the listening mechanism and the electrodes for terminating the transmission of the musical electric signals thereto after the cessation of a user-selected time interval.

1 Claim, 3 Drawing Sheets

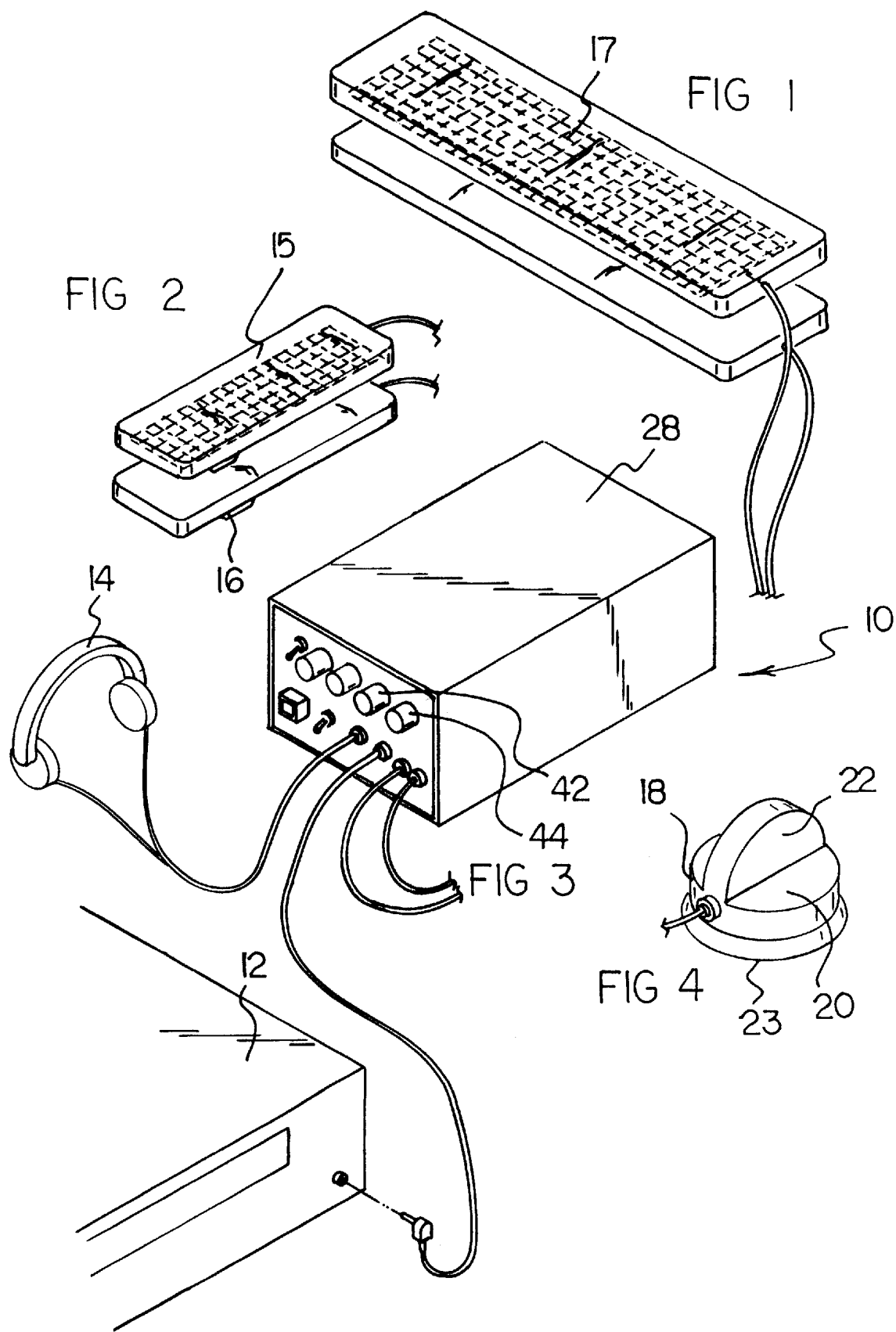

(1) 6,104,820

MUSICAL MASSAGER

BACKGROUND OF THE INVENTION

1. Field of the Invention

The present invention relates to massagers and more particularly pertains to a new musical massager for subjecting muscle tissue to electrical signals corresponding to audible music.

2. Description of the Prior Art

The use of massagers is known in the prior art. More specifically, massagers heretofore devised and utilized are known to consist basically of familiar, expected and obvious structural configurations, notwithstanding the myriad of designs encompassed by the crowded prior art which have been developed for the fulfillment of countless objectives and requirements.

Known prior art massagers include U.S. Pat. Nos. 4,779,615; 4,322,585; Des. 302,302; 4,791,673; 5,323,468; and 4,070,553.

In these respects, the musical massager according to the present invention substantially departs from the conventional concepts and designs of the prior art, and in so doing provides an apparatus primarily developed for the purpose of subjecting muscle tissue to electrical signals corresponding to audible music.

SUMMARY OF THE INVENTION

In view of the foregoing disadvantages inherent in the known types of massagers now present in the prior art, the present invention provides a new musical massager construction wherein the same can be utilized for subjecting muscle tissue to electrical signals corresponding to audible music.

The general purpose of the present invention, which will be described subsequently in greater detail, is to provide a new musical massager apparatus and method which has many of the advantages of the massagers mentioned heretofore and many novel features that result in a new musical massager which is not anticipated, rendered obvious, suggested, or even implied by any of the prior art massagers, either alone or in any combination thereof.

To attain this, the present invention generally comprises a music source adapted to generate a musical electric signal corresponding to music at an output thereof. A pair of headphones are adapted to be situated adjacent ears of a user and releasably connected to the music source for allowing the user to listen to the music. Shown in FIGS. 1 & 2 are a plurality of pads each having a planar top face, a planar bottom face, and a thin periphery formed therebetween having a rectangular configuration and defining an interior space. Each pad has an electrode situated within the interior space and adapted for subjecting human muscle tissue to the musical electric signal. The plurality of pads include a pair of small pads with a first width and a first length. Associated therewith is a pair of large pads with a second width and a second length that are larger than those of the small pads. FIG. 4 depicts a hand held pad having a disk-shaped base with a semicircular planar member. The semicircular planar member is coupled to a top face of the disk-shaped base along a diameter thereof and extends upwardly therefrom. A bottom surface has a cloth mounted thereon. The base houses an electrode. As shown in FIGS. 3 and 5 a control unit is provided including a sound actuated switch. The sound actuated switch includes an input removably connected to the music source and an output removably connected to the headphones. During use, the sound actuated switch has a first mode upon the lack of detection of ambient sound distant the headphones for allowing communication between the music source and headphones. The switch further has a second mode upon the detection of ambient sound distant the headphones for precluding communication between the music source and headphones. A pad intensity selection means is removably connected between the music source and the electrodes of the pads. The pad intensity selection means is adapted for increasing the magnitude of the musical electric signals transmitted to the electrodes of the pads by a first amount in a first orientation. In a second orientation, the musical electric signals are increased by a second greater amount. It should be noted that an augmented signal which corresponds to the music is available at the electrodes. Next provided is a head phone volume control dial for allowing a user to selectively determine the magnitude of the musical electric signals transmitted from the music source to the headphones. Connected between the music source and the headphones and the electrodes of the pads is an equalizer. The equalizer serves for allowing a user to select which frequencies of the musical electric signals being transmitted thereto are attenuated. Finally, a timer is connected between the music source and the head phones and the electrodes for ceasing the transmission of the musical electric signals thereto after the cessation of a user-selected time interval.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new musical massager apparatus and method which has many of the advantages of the massagers mentioned heretofore and many novel features that result in a new musical massager which is not anticipated, rendered obvious, suggested, or even implied by any of the prior art massagers, either alone or in any combination thereof.

It is another object of the present invention to provide a new musical massager which may be easily and efficiently manufactured and marketed.

It is a further object of the present invention to provide a new musical massager which is of a durable and reliable construction.

An even further object of the present invention is to provide a new musical massager which is susceptible of a low cost of manufacture with regard to both materials and labor, and which accordingly is then susceptible of low prices of sale to the consuming public, thereby making such musical massager economically available to the buying public.

Still yet another object of the present invention is to provide a new musical massager which provides in the apparatuses and methods of the prior art some of the advantages thereof, while simultaneously overcoming some of the disadvantages normally associated therewith.

Still another object of the present invention is to provide a new musical massager for subjecting muscle tissue to electrical signals corresponding to audible music.

Even still another object of the present invention is to provide a new musical massager that includes a music source adapted to generate a musical electric signal corresponding to music at an output thereof. A listening mechanism is adapted to be situated adjacent ears of a user and releasably connected to the music source for allowing the user to listen to the music. At least one pad is included for subjecting human muscle tissue to the musical electric signal. A control unit includes a timer connected between the music source and the listening mechanism and the electrodes for terminating the transmission of the musical electric signals thereto after the cessation of a user-selected time interval.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the large pads of a new musical massager according to the present invention.

FIG. 2 is a perspective view of the small pads of the present invention.

FIG. 3 is a perspective view of the control unit of the present invention.

FIG. 4 is a perspective view of the hand-held massager of the present invention.

DESCRIPTION OF THE PREFERRED EMBODIMENT

Figure 5:
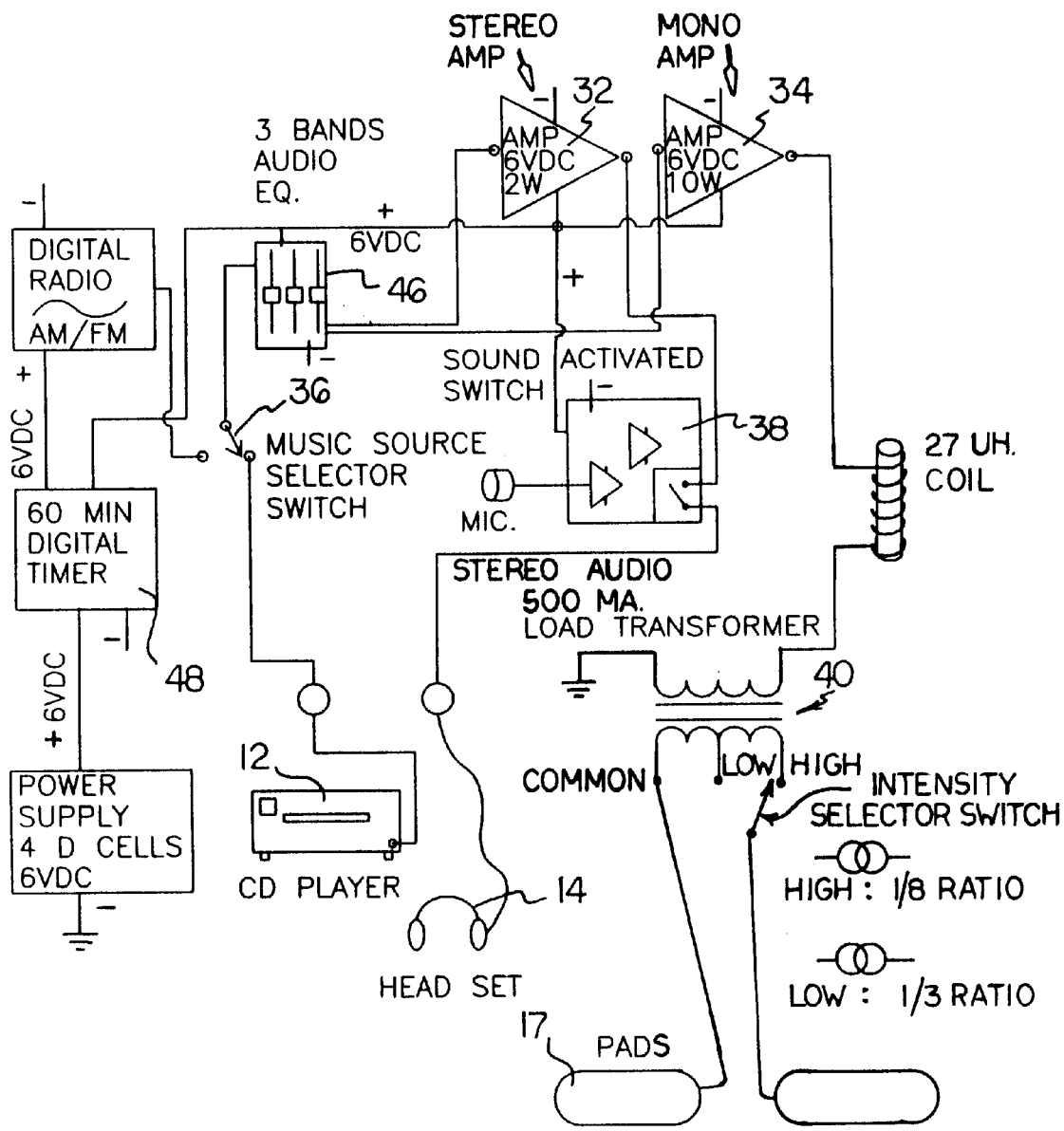
FIG. 5 is a schematic diagram of the present invention.

With reference now to the drawings, and in particular to FIGS. 1 through 6 thereof, a new musical massager embodying the principles and concepts of the present invention and generally designated by the reference numeral 10 will be described.

The present invention, as designated as numeral 10, includes a music source 12 adapted to generate a musical electric signal corresponding to music at an output thereof. Preferably, both a radio source and a playback mechanism, such as a compact disk player are provided. As an option, however, the present invention may include just a radio and an auxiliary jack for connection with a separate playback mechanism. As an option, a memory bank may be provided for storing the settings of the radio. A pair of headphones 14 are adapted to be situated adjacent ears of a user and releasably connected to the music source for allowing the user to listen to the music.

Shown in FIGS. 1 & 2 are a plurality of pads each having a planar top face, a planar bottom face, and a thin periphery formed therebetween having a rectangular configuration and defining an interior space. Each pad has an electrode situated within the interior space for subjecting human muscle tissue to the musical electric signal. The plurality of pads include a pair of small pads 15 with a first width and a first length. The bottom face of each of the small pads has at least one resting member 16. Associated therewith is a pair of large pads 17 with a second width and a second length that are larger than those of the small pads.

FIG. 4 depicts a hand held pad 18 having a disk-shaped base 20 with a semicircular planar member. The semicircular planar member 22 is coupled to a top face of the disk-shaped base along a diameter thereof and extends upwardly therefrom. A bottom surface has a cloth 23 mounted thereon. The base houses an electrode similar to the previous pads.

Figure 6:
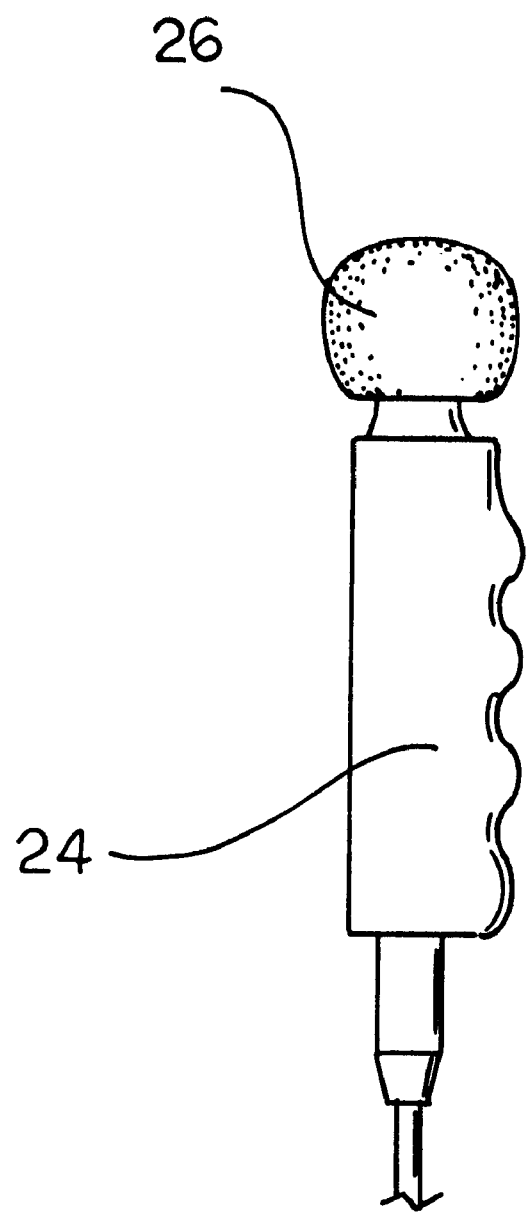
FIG. 6 is a perspective view of another hand held massager of the present invention.

FIG. 6 shows another hand held face pad including a generally cylindrically shaped grip 24. The grip has a plurality of linearly aligned undulations formed along a length thereof. A dome-shaped housing 26 is mounted to a top of the grip for containing an electrode. Similar to the previous embodiment, the present embodiment is equipped with a cloth that encompasses the dome-shaped housing. As such, the cloth may be wetted with water so as to allow electrical communication with skin of a user. It should be noted that at least two pads must always be in contact with the skin of the user for operation to be permitted.

As shown in FIGS. 3 and 5 a control unit 28 is provided. As shown in FIG. 5, the control unit includes a first amplifier 32 connected between the music source and the headphones for amplifying the musical electric signals to permit listening at an audible level. Further, a second amplifier 34 is connected between the music source and the electrodes of the pads such that an augmented signal which corresponds to the music is available at the electrodes. The control unit has a music source selection switch 36 for determining which of the music sources supplies the headphones and electrodes of the pads with the musical electric signals.

The control unit further includes a sound actuated switch 38 with an input removably connected to the music source and an output removably connected to the headphones. During use, the sound actuated switch has a first mode upon the lack of detection of ambient sound distant the headphones. In such mode, the sound actuated switch is adapted for allowing communication between the music source and headphones. The switch further has a second mode upon the detection of ambient sound distant the headphones for precluding communication between the music source and headphones. Note FIG. 5. Ideally, a noise switch is included for selecting a level at which the sound actuated switch switches to the second mode.

A pad intensity selection means 40 is removably connected between the music source and the electrodes of the pads. The pad intensity selection means is adapted for increasing the magnitude of the musical electric signals transmitted to the electrodes of the pads by a first amount in a first orientation. In a second orientation, the musical electric signals are increased by a second greater amount. For fine tuning the intensity of the signal provided by the electrodes, a pad intensity dial 42 is ideally connected in series with the pad intensity selection means.

Next provided is a head phone volume control dial 44 for allowing a user to selectively determine the magnitude of the musical electric signals transmitted from the music source to the headphones. Connected between the music source and the headphones and the electrodes of the pads is an equalizer 46. The equalizer serves for allowing a user to select which frequencies of the musical electric signals being transmitted thereto are attenuated.

Finally, a timer 48 is connected between the music source and the head phones and the electrodes for ceasing the transmission of the musical electric signals thereto after the cessation of a user-selected time interval. The time interval is preferably displayed on an LED digital display situated on the control unit.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A massaging musical device comprising, in combination:

a music source adapted to generate a musical electric signal corresponding to music at an output thereof;

a pair of headphones adapted to be situated adjacent ears of a user and releasably connected to the music source for allowing the user to listen to the music;

a plurality of pads each having a planar top face, a planar bottom face, and a thin periphery formed therebetween having a rectangular configuration and defining an interior space, each pad having an electrode within the interior space adapted for subjecting human muscle tissue to the musical electric signal, the plurality of pads including a pair of small pads with a first width and a first length and a pair of large pads with a second width and a second length that are larger than those of the small pads;

a hand held pad having a disk-shaped base with a semicircular planar member coupled to a top face of the disk-shaped base along a diameter thereof and extending upwardly therefrom, a bottom surface having a cloth mounted thereon, wherein the base houses an electrode; and a control unit including:

a sound actuated switch having an input removably connected to the music source and an output removably connected to the headphones, wherein the sound actuated switch has a first mode upon the lack of detection of ambient sound distant the headphones for allowing communication between the music source and headphones and a second mode upon the detection of ambient sound distant the headphones for precluding communication between the music source and headphones, pad intensity selection means removably connected between the music source and the electrodes of the pads for increasing the magnitude of the musical electric signals transmitted to the electrodes of the pads by a first amount in a first orientation and a second greater amount in a second orientation such that an augmented signal which corresponds to the music is available at the electrodes, a head phone volume control dial for allowing a user to selectively determine the magnitude of the musical electric signals transmitted from the music source to the headphones, an equalizer connected between the music source and the headphones and the electrodes of the pads for allowing a user to select which frequencies of the musical electric signals being transmitted thereto are attenuated, and a timer connected between the music source and the head phones and the electrodes for ceasing the transmission of the musical electric signals thereto after the cessation of a user-selected time interval.

* * * * *